(12) United States Patent
Ellson et al.

(10) Patent No.: US 6,932,097 B2
(45) Date of Patent: Aug. 23, 2005

(54) ACOUSTIC CONTROL OF THE COMPOSITION AND/OR VOLUME OF FLUID IN A RESERVOIR

(75) Inventors: Richard N. Ellson, Palo Alto, CA (US); Mitchell W. Mutz, Palo Alto, CA (US)

(73) Assignee: Picoliter Inc., Sunnyvale, CA (US)

( * ) Notice: Subject to any disclaimer, the term of this patent is extended or adjusted under 35 U.S.C. 154(b) by 409 days.

(21) Appl. No.: 10/175,374

(22) Filed: Jun. 18, 2002

(65) Prior Publication Data

US 2003/0230344 A1 Dec. 18, 2003

(51) Int. Cl.[7] ............................................. F16K 21/18
(52) U.S. Cl. ........................ 137/2; 137/391; 137/386; 73/290 V; 367/908
(58) Field of Search ................................. 137/391, 386, 137/2; 73/149, 290 V, 861.18, 861.25; 347/6, 7, 75; 367/908

(56) References Cited

U.S. PATENT DOCUMENTS

| | | | |
|---|---|---|---|
| 4,308,547 A | | 12/1981 | Lovelady et al. |
| 4,787,407 A | * | 11/1988 | Vogel .............................. 137/2 |
| 5,424,766 A | | 6/1995 | Anderson |
| 5,507,178 A | | 4/1996 | Dam |
| 5,520,715 A | | 5/1996 | Oeftering |
| 5,722,479 A | | 3/1998 | Oeftering |
| 5,798,779 A | | 8/1998 | Nakayasu et al. |
| 5,880,364 A | | 3/1999 | Dam |
| 6,003,388 A | * | 12/1999 | Oeftering .................. 73/864.01 |
| 6,044,694 A | | 4/2000 | Anderson et al. |
| 6,053,041 A | * | 4/2000 | Sinha ........................ 73/290 V |
| 6,263,731 B1 | * | 7/2001 | Getman et al. ............ 73/290 V |
| 2002/0037375 A1 | | 3/2002 | Ellson et al. |
| 2002/0037579 A1 | | 3/2002 | Ellson et al. |
| 2002/0064808 A1 | | 5/2002 | Mutz et al. |
| 2002/0064809 A1 | | 5/2002 | Mutz et al. |

FOREIGN PATENT DOCUMENTS

| | | |
|---|---|---|
| EP | 1208913 A2 | 5/2002 |
| EP | 1208914 A2 | 5/2002 |
| EP | 1209466 A2 | 5/2002 |
| WO | WO 98/15501 | 4/1998 |
| WO | WO 02/24325 | 3/2002 |

OTHER PUBLICATIONS

U.S. Appl. No. 09/669,194, filed Sep. 25, 2000, Ellson et al.
U.S. Appl. No. 09/669,996, filed Sep. 25, 2000, Ellson et al.
U.S. Appl. No. 10/010,972, filed Dec. 4, 2001, Mutz et al.
U.S. Appl. No. 10/112,693, filed Mar. 28, 2002, Ellson et al.
Amemiya et al. (1997), "Ink Jet Printing with Focused Ultrasonic Beams," *Proceedings of the IS&T's NIP13: 1997 International Conference on Digital Printing Technologies*, pp. 698–702.
Goldmann et al. (2000), "DNA–Printing: Utilization of a Standard Inkjet Printer for the Transfer of Nucleic Acids to Solid Supports," J. Biochem. Biophys. Methods 42:105–110.

* cited by examiner

*Primary Examiner*—Kevin Lee
(74) *Attorney, Agent, or Firm*—Reed Intellectual Property Law Group

(57) ABSTRACT

The invention provides a device for controlling the composition and/or volume of a fluid within a reservoir. The device includes a reservoir adapted to contain at least one fluid, a means for monitoring a characteristic of the fluid contained in the reservoir, and a means for introducing additional fluid into the reservoir according to the fluid characteristic monitored by the monitoring means. The device also includes an acoustic generator for generating acoustic radiation. A dispensing means may be provided as well. Other devices and methods that use acoustic radiation to control the composition and/or volume of a fluid within a reservoir are included.

61 Claims, 4 Drawing Sheets

US 6,932,097 B2

ACOUSTIC CONTROL OF THE COMPOSITION AND/OR VOLUME OF FLUID IN A RESERVOIR

TECHNICAL FIELD

The invention relates generally to the use of acoustic energy to control the composition and/or volume of a fluid within a reservoir. In particular, the invention relates to devices and methods for acoustically monitoring and adjusting the composition and/or volume of a fluid in a reservoir. The invention is particularly suited for use with a reservoir containing at least one fluid comprised of a plurality of constituents, wherein at least one constituent may be preferentially removed from the reservoir.

BACKGROUND

There exists a need in pharmaceutical, biotechnological, and other scientific industries to be able to quickly screen, identify, and/or process large numbers or varieties of fluids. As a result, much attention has been focused on developing combinatorial techniques that require efficient, precise, and accurate fluid handling methods. In order to achieve sufficient efficiency and precision, certain disadvantages inherent in conventional fluid handling systems must be overcome. For example, most fluid handling systems presently in use require that contact be established between the fluid to be transferred and an associated solid surface. Such contact typically results in surface wetting that represents a source of unavoidable fluid waste, a notable drawback when the fluid to be transferred is rare and/or expensive. In addition, a number of fluid dispensing systems are constructed using networks of tubing or other fluid transporting conduits. For example, air bubbles can be entrapped or particulates may become lodged in tubing networks, which, in turn, could compromise fluid transport performance and result in diminished or misdirected fluid flow.

Since fluids used in pharmaceutical, biotechnological, and other scientific industries may be rare and/or expensive, techniques capable of handling small volumes of fluids provide readily apparent advantages over those requiring relatively larger volumes. Typically, fluids for use in combinatorial methods are often provided as a collection or library of organic and/or biological compounds. In many instances, well plates are used to store a large number of fluids for screening and/or processing. Well plates are typically single piece in construction and comprise a plurality of identical wells, wherein each well is adapted to contain a small volume of fluid. Such well plates are commercially available in standardized sizes and may contain, for example, 96, 384, 1536, or 3456 wells per well plate.

Pipettes or similar devices are often employed to dispense fluids through an opening into or out of the interior of a well within a well plate. In some instances, complex robotic and/or automated systems may be configured to handle a large number of sample fluids. When a pipetting system is employed during extraction, a minimum loading volume may be required for the system to function properly. Similarly, other fluid dispensing systems may require a certain minimum reservoir volume to function properly. Thus, for any fluid dispensing system, it is important to monitor the reservoir composition and/or volume to determine whether a minimum amount of fluid is provided. Such content monitoring generally serves to indicate the overall performance of a fluid dispensing system, as well as to maintain the integrity of the combinatorial methods.

In addition, when a fluid in a reservoir is exposed to an uncontrolled environment, environmental effects may play a role in detrimentally altering the reservoir composition and/or volume. For example, when a solvent with a low boiling point is used to dissolve or suspend a compound of interest, evaporation of the solvent from the reservoir increases the concentration of compound therein. This, in turn, may cause dissolved compounds to precipitate out of solution, or suspended particles to agglomerate. Thus, for example, when tubing is employed, such precipitation and/or agglomeration may clog the tubing network. Conversely, dimethylsulfoxide (DMSO) is a common organic solvent employed to dissolve or suspend compounds commonly found in drug libraries. DMSO is highly hygroscopic and tends to absorb any ambient water with which it comes into contact. In turn, the absorption of water dilutes the concentration of the compounds as well as alters the ability of the DMSO to suspend the compounds. Furthermore, the absorption of water may promote the decomposition of water-sensitive compounds.

Acoustic technologies may be advantageously employed in fluid handling applications and have been described in a number of patents. For example, U.S. Pat. No. 4,308,547 to Lovelady et al. describes a liquid drop emitter that utilizes acoustic radiation to eject droplets from a body of liquid onto a moving document to result in the formation of characters or barcodes thereon. A nozzleless inkjet printing apparatus is used such that controlled drops of ink are propelled by an acoustical force produced by a curved transducer at or below a free surface of the ink. More recently, acoustic ejection has been employed in contexts other than ink printing applications. For example, U.S. patent application Publication No. 20020037579 to Ellson et al. describes the use of focused acoustic radiation to dispense fluids with sufficient accuracy and precision to prepare biomolecular arrays from a plurality of reservoirs.

Acoustic radiation has also been used to assess the composition and/or volume of one or more fluid reservoirs. For example, U.S. Pat. No. 5,507,178 to Dam describes a sensor for determining the presence of a liquid and for identifying the type of liquid in a container. The ultrasonic sensor determines the presence of the liquid through an ultrasonic liquid presence sensing means, and identifies the type of liquid through a liquid identification means that includes a pair of electrodes and an electrical pulse generating means. This device suffers from the disadvantage that the sensor must be placed in contact with the liquid.

U.S. Pat. No. 5,880,364 to Dam, on the other hand, describes a non-contact ultrasonic system for measuring the volume of liquid in a plurality of containers. An ultrasonic sensor is disposed opposite the top of the containers. A narrow beam of ultrasonic radiation is transmitted from the sensor to the open top of an opposing container to be reflected from the air-liquid interface of the container back to the sensor. By using the round trip transit time of the radiation and the dimensions of the containers being measured, the volume of liquid in the container can be calculated. The device lacks precision because air is a poor conductor of acoustic energy, particularly at the high frequencies required to produce the small wavelengths beneficial to precision measurements. Thus, while this device may provide a rough estimate of the volume of liquid in relatively large containers, it is unsuitable for providing a detailed assessment of the composition and/or volume of small volume reservoirs that are typically used in combinatorial techniques. In particular, this device cannot determine the position of the bottoms of containers since substantially all of the emitted acoustic energy is reflected from the liquid surface and does not penetrate sufficiently to detect the bottom. Small volume reservoirs such as those found in well plates are regular arrays of fluid containers, and the location of the container bottom can vary by a significant fraction of the nominal height of a container due to bow in the plate. In short, detection of only the position of the liquid surface leads to significant errors in height and thus volume estimation in common containers.

More recently, U.S. patent application Ser. No. 10/010, 972, "Acoustic Assessment of Fluids in a Plurality of Reservoirs," inventors Mutz, Ellson, and Foote, filed Dec. 7, 2001, describes the use of an acoustic generator to generate acoustic radiation used to eject fluid from a reservoir or to analyze a property of the fluid content within the reservoir. By analyzing a characteristic of the acoustic radiation transmitted through the fluid, various properties of the fluid within the reservoir may be determined. In addition, such analysis may be carried out to determine the spatial relationship between a free surface of the fluid within the reservoir.

Because dispensation accuracy, precision, and repeatability often depend upon the source from which a fluid is dispensed, there exists a need in the art to control the composition and/or volume of fluid reservoirs. This need is present in various fluid dispensing techniques that involve the handling of small volumes of fluid (e.g., pipettes, capillaries, inkjet printheads, etc.), and is particularly significant when focused acoustic radiation is employed to eject droplets of fluid from a reservoir. Such precise control allows increased robustness, efficiency, and effectiveness of fluid delivery, which is especially valuable for processes such as combinatorial techniques, microfluidic applications, nucleotidic analyses, proteomic studies, and cellular assays.

SUMMARY OF THE INVENTION

In a first embodiment, the invention provides a device for controlling the composition and/or volume of a fluid within a reservoir. The device includes a reservoir adapted to contain a fluid, a means for monitoring a particular characteristic of the fluid contained in the reservoir, and an introducing means for introducing additional fluid into the reservoir according to the fluid characteristic monitored by the monitoring means. The device also includes an acoustic generator for generating acoustic radiation associated with the monitoring means, the introducing means, or both. The monitoring means typically does not directly contact fluid contained in the reservoir.

When the acoustic generator is associated with the monitoring means, the monitoring means further includes an analyzer for analyzing acoustic radiation generated by the acoustic generator. Typically, the analyzer is positioned to receive acoustic radiation generated by the acoustic generator and transmitted through any fluid contained in the reservoir. Optimally, the analyzer is positioned to receive acoustic radiation reflected by a free surface of any fluid contained in the reservoir. In such a case, the analyzer may share a common component, e.g., a piezoelectric element, with the acoustic generator.

Optionally, a dispensing means for dispensing fluid from the reservoir is also provided. The dispensing means may employ acoustic dispensing technologies such as acoustic ejectors, which employ a focusing means for focusing acoustic radiation generated by the acoustic generator.

In another embodiment, the invention provides a device for dispensing fluid from a reservoir. The device includes an acoustic generator for generating acoustic radiation, reservoir adapted to contain a fluid, a dispensing means for controllably dispensing the fluid from the reservoir without direct contact with any fluid in the reservoir, a monitoring means for monitoring a characteristic of any fluid contained in the reservoir, and an introducing means for introducing additional fluid into the reservoir according to the fluid characteristic monitored by the monitoring means. At least two of the dispensing means, the monitoring means, and the introducing means are associated with the acoustic generator.

In a further embodiment, the invention relates to a method for controlling the composition and/or volume of a fluid within a reservoir, which involves monitoring a characteristic of a fluid contained in a reservoir without directly contacting the fluid, then introducing additional fluid into the reservoir according to the monitored fluid characteristic. In some instances, the fluid characteristic is monitored acousticly, in which case, the inventive method may involve generating acoustic radiation such that the radiation interacts with the fluid contained in the reservoir, then analyzing the acoustic radiation after interaction with the fluid to assess the fluid characteristic being monitored. For example, the acoustic radiation generated by the acoustic generator may be transmitted through the fluid in the reservoir and analyzed after interaction with the fluid. Optionally, the acoustic radiation may be analyzed after reflection by a free fluid surface within the reservoir.

In addition or in the alternative, additional fluid may be introduced into the reservoir using an acoustic introducing means. In such a case, acoustic radiation may be applied to a source of additional fluid in a manner effective to transport additional fluid into the reservoir.

In a still further embodiment, the invention relates to a method for controlling the composition and/or volume of a fluid within a reservoir. The method involves monitoring for preferential removal of at least one constituent from a reservoir containing a fluid comprised of a plurality of constituents, and introducing additional fluid comprised of the at least one constituent into the reservoir in response to any preferential removal of the at least one constituent as monitored. In some instances, the method involves using acoustic radiation to monitor for preferential removal one or more constituents in the reservoir over another. In addition or in the alternative, additional fluid may be introduced into the reservoir through the use of acoustic radiation.

For any of the inventive devices and methods, a plurality of fluid reservoirs may be provided. In such a case, the composition and/or volume of each of the reservoirs may be monitored and controlled using the same monitoring means and the same introducing means.

BRIEF DESCRIPTION OF THE DRAWINGS

FIG. 1A shows the acoustic analyzer/ejector acoustically coupled to the first reservoir engaged in the acoustic monitoring of the composition and/or volume within the reservoir. FIG. 1B illustrates the removal of a cover from the reservoirs and the activation of the analyzer ejector in order to eject a droplet of fluid from within the first reservoir toward a first designated site on a substrate surface to form an array. FIG. 1C shows the acoustic analyzer/ejector acoustically coupled to a second reservoir to monitor the composition and/or volume within the reservoir as a result. FIG. 1D illustrates the replenishment of evaporated fluid from the second reservoir. FIG. 1E illustrates the activation of the ejector in order to eject a droplet of fluid from within the second reservoir toward a second designated site on a substrate surface.

DETAILED DESCRIPTION OF THE INVENTION

Figure 1A:
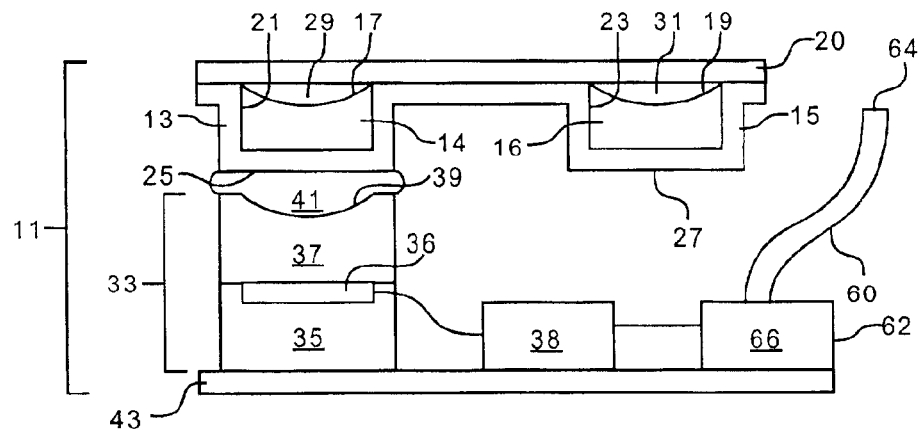
FIGS. 1A–1E, collectively referred to as FIG. 1, schematically illustrate in simplified cross-sectional view a preferred embodiment of the inventive device that allows the acoustic assessment in reflective mode of the composition and/or volume of a plurality of reservoirs and the introduction of fluid into the reservoirs. As depicted, the device comprises first and second reservoirs, a combined acoustic analyzer/ejector, and a positioning means.
Figure 1B:
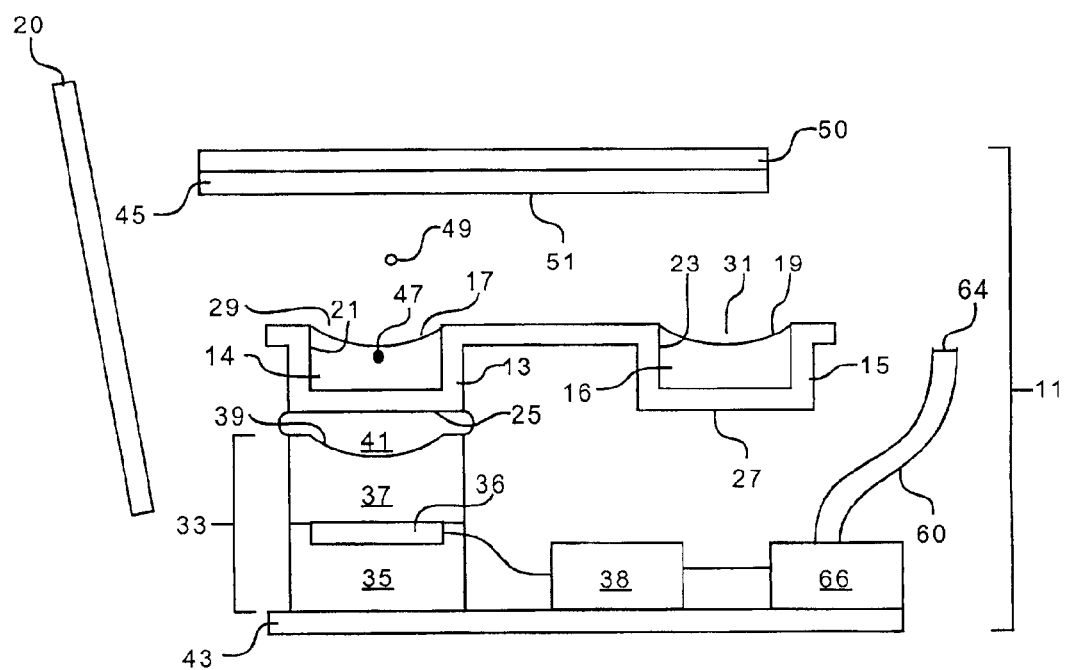
Figure 1C:
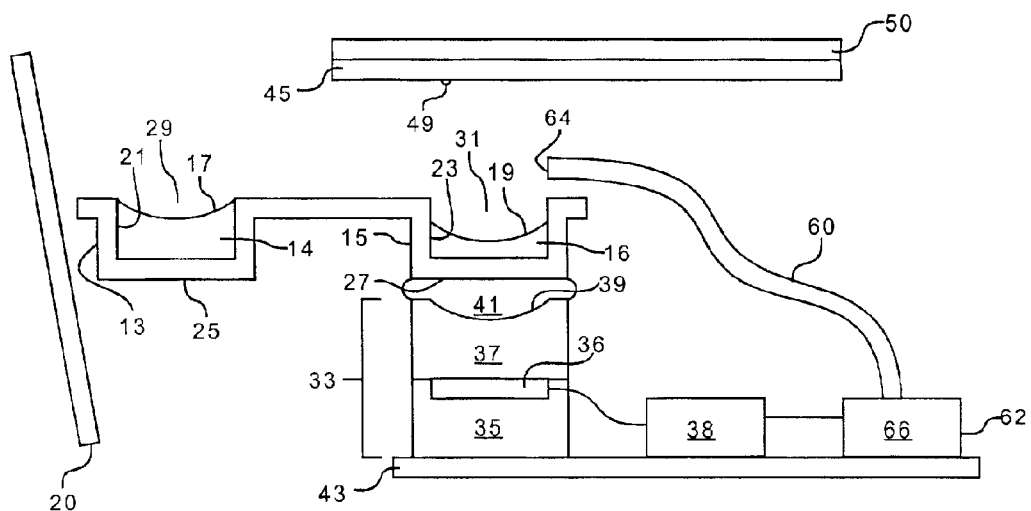
Figure 1D:
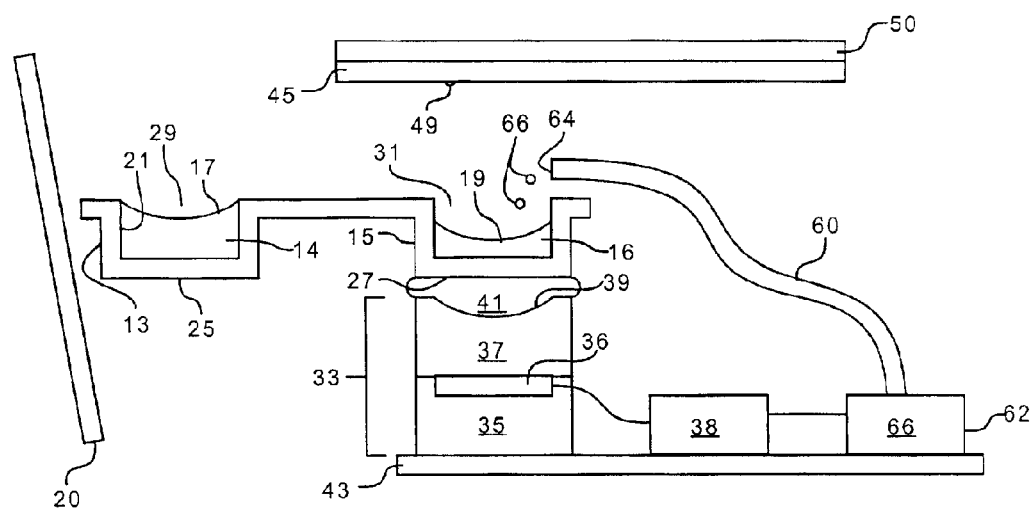

Before describing the present invention in detail, it is to be understood that this invention is not limited to specific fluids, biomolecules, or device structures, as such may vary. It is also to be understood that the terminology used herein is for the purpose of describing particular embodiments only, and is not intended to be limiting.

It must be noted that, as used in this specification and the appended claims, the singular forms "a," "an," and "the" include plural referents unless the context clearly dictates otherwise. Thus, for example, reference to "a reservoir" includes a plurality of reservoirs, reference to "a fluid" includes a plurality of fluids, reference to "a characteristic" includes a combination of characteristics, and the like.

In describing and claiming the present invention, the following terminology will be used in accordance with the definitions set forth below.

The terms "acoustic coupling" and "acoustically coupled" as used herein refer to a state wherein an object is placed in direct or indirect contact with another object so as to allow acoustic radiation to be transferred between the objects without unacceptable loss of acoustic energy. When two entities are indirectly acoustically coupled, an "acoustic coupling medium" is needed to provide an intermediary through which acoustic radiation may be transmitted. Thus, an ejector may be acoustically coupled to a fluid, such as by immersing the ejector in the fluid, or by interposing an acoustic coupling medium between the ejector and the fluid, in order to transfer acoustic radiation generated by the ejector through the acoustic coupling medium and into the fluid.

The terms "acoustic radiation" and "acoustic energy" are used interchangeably herein and refer to the emission and propagation of energy in the form of sound waves. As with other waveforms, acoustic radiation may be focused using a focusing means, as discussed below.

The term "attached," as in, for example, a substrate surface having a moiety "attached" thereto, includes covalent and noncovalent binding, adsorption, and physical immobilization. The terms "binding" and "bound" are identical in meaning to the term "attached."

The term "array" as used herein refers to a two-dimensional arrangement of features, such as an arrangement of reservoirs (e.g., wells in a well plate) or an arrangement of different moieties, including ionic, metallic, or covalent crystalline, e.g., molecular crystalline, composite or ceramic, glassine, amorphous, fluidic or molecular materials on a substrate surface (as in an oligonucleotide or peptidic array). Arrays are generally comprised of regular, ordered features, as in, for example, a rectilinear grid, parallel stripes, spirals, and the like, but non-ordered arrays may be advantageously used as well. An array is distinguished from the more general term "pattern" in that patterns do not necessarily contain regular and ordered features.

The terms "biomolecule" and "biological molecule" are used interchangeably herein to refer to any organic molecule that is, was, or can be a part of a living organism, regardless of whether the molecule is naturally occurring, recombinantly produced, or chemically synthesized in whole or in part. The terms encompass, for example, nucleotides, amino acids, and monosaccharides, as well as oligomeric and polymeric species, such as oligonucleotides and polynucleotides, peptidic molecules, such as oligopeptides, polypeptides and proteins, saccharides such as disaccharides, oligosaccharides, polysaccharides, mucopolysaccharides or peptidoglycans (peptidopolysaccharides) and the like. The terms also encompass ribosomes, enzyme cofactors, pharmacologically active agents, and the like. Additional information relating to the term "biomolecule" can be found in U.S. patent application Publication No. 20020037579 to Ellson et al.

The term "fluid" as used herein refers to matter that is nonsolid, or at least partially gaseous and/or liquid, but not entirely gaseous. A fluid may contain a solid that is minimally, partially, or fully solvated, dispersed, or suspended. Examples of fluids include, without limitation, aqueous liquids (including water per se and salt water) and nonaqueous liquids such as organic solvents and the like. As used herein, the term "fluid" is not synonymous with the term "ink" in that an ink must contain a colorant and may not be gaseous.

The terms "focusing means" and "acoustic focusing means" refer to a means for causing acoustic waves to converge at a focal point, either by a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as are known in the art and described, for example, in U.S. Pat. No. 5,798,779 to Nakayasu et al. and Amemiya et al. (1997) *Proceedings of the 1997 IS&T NIP13 International Conference on Digital Printing Technologies*, pp. 698–702.

The terms "library" and "combinatorial library" are used interchangeably herein to refer to a plurality of chemical or biological moieties arranged in a pattern or an array such that the moieties are individually addressable. In some instances, the plurality of chemical or biological moieties is present on the surface of a substrate, and in other instances, the plurality of moieties represents the composition and/or volume of a plurality of reservoirs. Preferably, but not necessarily, each moiety is different from each of the other moieties. The moieties may be, for example, peptidic molecules and/or oligonucleotides.

The term "moiety" refers to any particular composition of matter, e.g., a molecular fragment, an intact molecule (including a monomeric molecule, an oligomeric molecule, and a polymer), or a mixture of materials (for example, an alloy or a laminate).

"Optional" or "optionally" means that the subsequently described circumstance may or may not occur, so that the description includes instances where the circumstance occurs and instances where it does not.

The term "reservoir" as used herein refers to a receptacle or chamber for containing a fluid. In some instances, a fluid contained in a reservoir necessarily will have a free surface, e.g., a surface that allows acoustic radiation to be reflected therefrom or a surface from which a droplet may be acoustically ejected. A reservoir may also be a locus on a substrate surface within which a fluid is constrained.

The term "substrate" as used herein refers to any material having a surface onto which one or more fluids may be deposited. The substrate may be constructed in any of a number of forms including, for example, wafers, slides, well plates, or membranes. In addition, the substrate may be porous or nonporous as required for deposition of a particular fluid. Suitable substrate materials include, but are not limited to, supports that are typically used for solid phase chemical synthesis, such as polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, and divinylbenzene styrene-based polymers), agarose (e.g., Sepharose®), dextran (e.g., Sephadex®), cellulosic polymers and other polysaccharides, silica and silica-based materials, glass (particularly controlled pore glass, or "CPG") and functionalized glasses, ceramics, such substrates treated with surface coatings, e.g., with microporous polymers (particularly cellulosic polymers such as nitrocellulose), microporous metallic compounds (particularly microporous aluminum) antibody-binding proteins (available from Pierce Chemical Co., Rockford Ill.), bisphenol A polycarbonate, or the like. Additional information relating to the term "substrate" can be found in U.S. patent application Publication No. 20020037579 to Ellson et al.

The term "substantially" as in, for example, "substantially identical volume" refers to volumes that differ by no more than 10%, preferably at least 5%, more preferably at least 1%, and most preferably at least 0.1%. Other uses of the term "substantially" involve an analogous definition.

The invention accordingly relates to the use of acoustic radiation to control the composition and/or volume of one or more fluid reservoirs. When a reservoir containing a fluid is provided, the invention involves monitoring a characteristic of fluid contained in the reservoir. Typically, the fluid characteristic is monitored acoustically using a monitoring means that does not directly contact any fluid contained in the reservoir. Additional fluid may be introduced into the reservoir using acoustic radiation as well. The invention is particularly useful in maintaining the concentration of solutes and the solvent composition of a reservoir within certain predetermined bounds. As a result, the invention enables more precise transfer of fluids. In addition, due to the precision and accuracy associated with acoustic technology, the device is particularly suited for controlling the composition and/or volume of small volume reservoirs.

In one embodiment, the invention provides a device that includes a reservoir, a monitoring means for monitoring a characteristic of any fluid contained in the reservoir, and an introducing means for introducing additional fluid into the reservoir according to the fluid characteristic monitored by the monitoring means. In some instances, the device may further include a dispensing means for controllably dispensing fluid from the reservoir. Although focused acoustic radiation may be used to dispense fluid from the reservoir, other types of focused radiation, e.g., electromagnetic radiation, may be used as well.

Thus, acoustic radiation may be used to dispense fluid from a reservoir, monitor the composition and/or volume of the reservoir, and/or introduce additional fluid into the reservoir. Accordingly, the monitoring means, the introducing means, and/or the dispensing means may use an acoustic generator for generating acoustic radiation. That is, an acoustic generator may be associated with the dispensing means, the monitoring means, and/or the introducing means. Optimally, the device is comprised of a single acoustic generator.

When the acoustic generator is associated with the monitoring means, the monitoring means may further include an analyzer for analyzing acoustic radiation generated by the acoustic generator. In such a case, the analyzer is typically positioned to receive acoustic radiation generated by the acoustic generator and transmitted through any fluid contained in the reservoir. Optimally, the analyzer is positioned to receive acoustic radiation reflected by a free surface of any fluid or by a fluid interface contained in the reservoir. In such a case, the analyzer may share a common component, such as a piezoelectric element, with the acoustic generator. For example, an acoustic monitoring means and analyzer such as those described in U.S. patent application Ser. No. 10/010,972 may be used with the present invention.

Such a device may also be used to control the composition and/or volume of a plurality of fluids, immiscible or otherwise, in one or more reservoirs. In the case where a plurality of reservoirs are provided, each may be adapted to contain the same fluid or different fluids. In addition, the monitoring means may be adapted to monitor a characteristic of fluid contained in each reservoir, and an introducing means may be adapted to introduce additional fluid into any selected reservoir according to the fluid characteristic of fluid contained in the selected reservoir as monitored by the monitoring means. Typically, the monitoring means is adapted to monitor the characteristic of fluid contained in a single reservoir at a time. For the case of a plurality of immiscible fluids within a single reservoir, the monitoring means may be adapted to monitor a characteristic of at least one of the immiscible fluids in the reservoir, and the introducing means may be adapted to introduce additional fluid of the appropriate type(s) according to the fluid characteristic monitored by the monitoring means.

FIG. 1 illustrates such an embodiment of the inventive device in simplified cross-sectional view and its use in depositing droplets of fluid onto a substrate surface. In this embodiment, the inventive device allows for control over the composition and/or volume of a plurality of reservoirs as well as acoustic ejection of fluid droplets from the reservoirs. The inventive device is shown in operation to form a biomolecular fluid array on a substrate surface. As with all figures referenced herein, in which like parts are referenced by like numerals, FIG. 1 is not to scale, and certain dimensions may be exaggerated for clarity of presentation. The device 11 includes a plurality of reservoirs, i.e., at least two reservoirs, with a first reservoir indicated at 13 and a second reservoir indicated at 15. As depicted, the reservoirs 13 and 15 are wells in a well plate, but this is not a necessity. In some instances, the plurality of reservoirs may be arranged in an array. In addition, the reservoirs may be provided as separate removable components.

As shown, the first reservoir 13 contains a first fluid 14, and the second reservoir 15 contains a second fluid 16.

Fluids 14 and 16 each have a fluid surface respectively indicated at 17 and 19. Fluids 14 and 16 may be the same or different, but each typically contains one or more biomolecules. In addition, the reservoirs are depicted as of substantially identical construction so as to be substantially acoustically indistinguishable, but identical construction is not a requirement. Each of the reservoirs 13 and 15 may be axially symmetric as shown, having vertical walls 21 and 23 extending upward from circular reservoir bases 25 and 27 and terminating at openings 29 and 31, respectively, although other reservoir shapes may be used. The material and thickness of each reservoir base should be such that acoustic radiation may be transmitted therethrough and into the fluid contained within the reservoirs. Optionally, a cover 20 is provided over the reservoirs so as to seal fluids 14 and 16 within the reservoirs 13 and 15, respectively.

The device also includes an acoustic ejector 33 comprised of an acoustic generator 35 for generating acoustic radiation and a focusing means 37 for focusing the acoustic radiation at a focal point within the fluid from which a droplet is to be ejected near the fluid surface. The acoustic generator contains a transducer 36, e.g., a piezoelectric element, commonly shared by an analyzer. As shown, a combination unit 38 is provided that both serves as a controller and a component of an analyzer. Operating as a controller, the combination unit 38 provides the piezoelectric element 36 with electrical energy that is converted into mechanical and acoustic energy. Operating as a component of an analyzer, the combination unit receives and analyzes electrical signals from the transducer. The electrical signals are produced as a result of the absorption and conversion of mechanical and acoustic energy by the transducer.

As shown in FIG. 1, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from each of the fluid surfaces 17 and 19 when acoustically coupled to reservoirs 13 and 15, and thus to fluids 14 and 16, respectively. The acoustic generator 35 and the focusing means 37 may function as a single unit controlled by a single controller, or they may be independently controlled, depending on the desired performance of the device. Typically, single ejector designs are preferred over multiple ejector designs because accuracy of droplet placement, and consistency in droplet size and velocity are more easily achieved with a single ejector.

There are also a number of ways to acoustically couple the ejector 33 to each individual reservoir and thus to the fluid therein. One such approach is through direct contact as is described, for example, in U.S. Pat. No. 4,308,547 to Lovelady et al., wherein a focusing means constructed from a hemispherical crystal having segmented electrodes is submerged in a liquid to be ejected. The aforementioned patent further discloses that the focusing means may be positioned at or below the surface of the liquid. This approach for acoustically coupling the focusing means to a fluid is undesirable, however, when the ejector is used to eject different fluids in a plurality of containers or reservoirs, as repeated cleaning of the focusing means would be required in order to avoid cross-contamination. The cleaning process would necessarily lengthen the transition time between each droplet ejection event. Also, in such a method, fluid would adhere to the ejector as it is removed from each container, wasting material that may be costly or rare.

Thus, a preferred approach would be to acoustically couple the ejector to the reservoirs and reservoir fluids without contacting any portion of the ejector, e.g., the focusing means, with any of the fluids to be ejected. To this end, as illustrated in FIG. 1, the present invention provides an ejector positioning means 43 for positioning the ejector in controlled and repeatable acoustic coupling with each of the fluids in the reservoirs to eject droplets therefrom without submerging the ejector therein. This typically involves direct or indirect contact between the ejector and the external surface of each reservoir. When direct contact is used in order to acoustically couple the ejector to each reservoir, it is preferred that the direct contact be wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs having a specially formed inverse surface.

Optimally, acoustic coupling is achieved between the ejector and each of the reservoirs through indirect contact, as illustrated in FIG. 1A. In this figure, an acoustic coupling medium 41 is placed between the ejector 33 and the base 25 of reservoir 13, with the ejector and reservoir located at a predetermined distance from each other. The acoustic coupling medium may be an acoustic coupling fluid, preferably an acoustically homogeneous material in conformal contact with both the acoustic focusing means 37 and each reservoir. In addition, it is important to ensure that the fluid medium is substantially free of material having different acoustic properties than the fluid medium itself. Furthermore, it is preferred that the acoustic coupling medium be comprised of a material having acoustic properties that facilitate the transmission of acoustic radiation without significant attenuation in acoustic pressure and intensity. Also, the acoustic impedance of the coupling medium should facilitate the transfer of energy from the coupling medium into the container. As shown, the first reservoir 13 is acoustically coupled to the acoustic focusing means 37, such that an acoustic wave is generated by the acoustic generator 35 and directed by the focusing means 37 into the acoustic coupling medium 41, which then transmits the acoustic radiation into the reservoir 13.

As discussed above, the inventive device also includes an introducing means 60. As depicted in FIG. 1, the introducing means 60 allows fluid to be transported from a source 62 of additional fluid 66 into the reservoirs via outlet 64. The introducing means is controlled by combination unit 38 and may be positioned by the ejector positioning means 43 or a separate additional fluid positioning means (not shown). Thus, for example, the introducing means 60 may allow fluid to be transported into a reservoir to which ejector 33 is acoustically coupled.

In operation, the acoustic ejector 33 is positioned by ejector positioning means 43, shown below reservoir 13, in order to achieve acoustic coupling between the ejector and the reservoir through acoustic coupling medium 41. Once the ejector, the reservoir, and the substrate are in proper alignment, the acoustic generator 35, as depicted in FIG. 1A, is activated to produce acoustic radiation that is directed toward a free fluid surface 17 of the first reservoir. The acoustic radiation will then travel in a generally upward direction toward the free fluid surface 17. The acoustic radiation will be reflected under different circumstances.

Typically, reflection will occur when there is a change in the acoustic property of the medium through which the acoustic radiation is transmitted. It has been observed that a portion of the acoustic radiation traveling upward will be reflected from the reservoir bases 25 and 27 as well as the free surfaces 17 and 19 of the fluids sealed within reservoirs 13 and 15.

The reflected acoustic radiation may be then employed for analyzing a characteristic of the fluid within reservoir 13. The acoustic generator is typically activated so as to generate low energy acoustic radiation that is insufficiently energetic to eject a droplet from the fluid surface 17. This is typically accomplished by using an extremely short pulse (on the order of tens of nanoseconds) relative to that required for droplet ejection (on the order of microseconds). By determining the time it takes for the acoustic radiation to be reflected by the fluid surface 17 back to the acoustic generator 35, for example, and then correlating that time with the speed of sound in the fluid, the distance—and thus the fluid height—may be calculated. Of course, care must be taken in order to ensure that the acoustic radiation reflected by the interface between the reservoir base and the fluid is discounted.

It will be appreciated by those of ordinary skill in the art that conventional or modified sonar techniques may be employed. Thus, the acoustic radiation will be reflected back at the piezoelectric element 36, where the acoustic energy will be converted into electrical energy for analysis. The analysis may be used, for example, to reveal whether the reservoir contains any fluid at all. If fluid is present in the reservoir, the location and the orientation of the free fluid surface within the reservoir may be determined, as well as the overall volume of the fluid. Characteristics of the reflected acoustic radiation may be analyzed in order to assess the spatial relationship between the acoustic generator and the fluid surface, the spatial relationship between a solid surface of the reservoir and the fluid surface, as well as to determine a characteristic of the fluid in each reservoir such as volume, viscosity, surface tension, acoustic impedance, acoustic attenuation, solid content, and impurity content. It should be noted that a fluid in a reservoir may be inhomogeneous and/or contain multiple phases of materials. For example, a fluid may entrain gaseous bubbles, emulsions of immiscible liquids, or suspended particulate matter. In such instances, acoustic radiation may be used to detect such inhomogenities. Thus, it is evident that the fluid characteristic to be determined by the invention may, in some cases, be a fluid property. Once the analysis has been performed, a decision may be made as to whether and/or how to dispense fluid from the reservoir.

In order to deposit droplets of fluid from the reservoirs on a substrate surface using the inventive device, substrate 45 is positioned above and in proximity to the first reservoir 13 such that one surface of the substrate, shown in FIG. 1 as underside surface 51, faces the reservoir and is substantially parallel to the surface 17 of the fluid 14 therein. As depicted in FIG. 1B, the ejector, the reservoir, and the substrate are positioned in proper alignment, and the cover 20 is removed from the reservoirs 13 and 15. Upon removal of the cover 20 from the reservoir 13, and before fluid 14 has an opportunity to evaporate from reservoir 13, the acoustic generator 35 is activated to produce acoustic radiation that is directed by the focusing means 37 to a focal point 47 near the fluid surface 17 of the first reservoir. That is, an ejection acoustic wave having a focal point near the fluid surface is generated in order to eject at least one droplet of the fluid, wherein the optimum intensity and directionality of the ejection acoustic wave is determined from the aforementioned analysis, optionally in combination with additional data. The "optimum" intensity and directionality are generally selected to produce droplets of consistent size and velocity. For example, the desired intensity and directionality of the ejection acoustic wave may be determined by using the data from the above-described assessment relating to reservoir volume or fluid property data, as well as geometric data associated with the reservoir. In addition, the data may show the need to reposition the ejector so as to reposition the acoustic generator with respect to the fluid surface, in order to ensure that the focal point of the ejection acoustic wave is near the fluid surface where desired. For example, if analysis reveals that the acoustic generator is positioned such that the ejection acoustic wave cannot be focused near the fluid surface, the acoustic generator is repositioned using vertical, horizontal, and/or rotational movement to allow appropriate focusing of the ejection acoustic wave.

As a result, droplet 49 is ejected from the fluid surface 17 onto a designated site on the underside surface 51 of the substrate. The ejected droplet may be retained on the substrate surface by solidifying thereon after contact; in such an embodiment, it may be necessary to maintain the substrate at a low temperature, i.e., a temperature that results in droplet solidification after contact. Alternatively, or in addition, a molecular moiety within the droplet attaches to the substrate surface after contact through adsorption, physical immobilization, or covalent binding.

Then, as shown in FIG. 1C, a substrate positioning means 50 repositions the substrate 45 over reservoir 15 in order to receive a droplet therefrom at a second designated site. FIG. 1C also shows that the ejector 33 has been repositioned by the ejector positioning means 43 below reservoir 15 and in acoustically coupled relationship thereto by virtue of acoustic coupling medium 41. Once properly aligned, the acoustic generator 35 of ejector 33 is activated to produce low energy acoustic radiation to assess the composition and/or volume of the reservoir 15 and to determine whether and/or how to eject fluid from the reservoir. Historical droplet ejection data associated with the ejection sequence may be employed as well. Again, there may be a need to reposition the ejector so as to reposition the acoustic generator with respect to the fluid surface, in order to ensure that the focal point of the ejection acoustic wave is near the fluid surface where desired. Should the results of the assessment indicate that fluid may be dispensed from the reservoir, focusing means 37 is employed to direct higher energy acoustic radiation to a focal point 48, as depicted in FIG. 1E, within fluid 16 near the fluid surface 19, thereby ejecting droplet 53 onto the substrate 45.

In some instances, fluid evaporation may take place from reservoir 15 after the removal of cover 20 therefrom. When the fluid 16 in reservoir 15 is a liquid containing a single constituent, e.g., water, evaporation of fluid 16 from the reservoir 15 does not alter the composition of the fluid 16 remaining in the reservoir, only the volume and height of the fluid remaining in the reservoir. Thus, the monitoring means may be adapted to monitor the change in height of fluid 16 and the associated "movement" of surface 19 toward the base 27 of reservoir 15. An example of acoustical monitoring the evaporation of water from a single well in a well plate comprised of 1536 wells is shown in FIG. 3, discussed further, infra.

FIGS. 1C and 1D depict a situation such that a quantity of fluid 16 has evaporated from reservoir 15. Such evaporation may occur as a result of the removal of cover 20 from reservoir 15, as depicted in FIG. 1B, and the time associated with ejection of fluid from reservoir 13. Such evaporation is revealed as the result of the assessment depicted in FIG. 1C. As a consequence, introducing means 60 is activated so as to transport fluid 66 from the source 62 of additional fluid into reservoir 15 via outlet 64. Once an appropriate quantity of additional fluid is introduced into reservoir 15, the ejector 33, as depicted in FIG. 1E, is activated to eject a droplet from the reservoir 15 onto the second designated site on the substrate surface 51.

Figures 1E, 2:
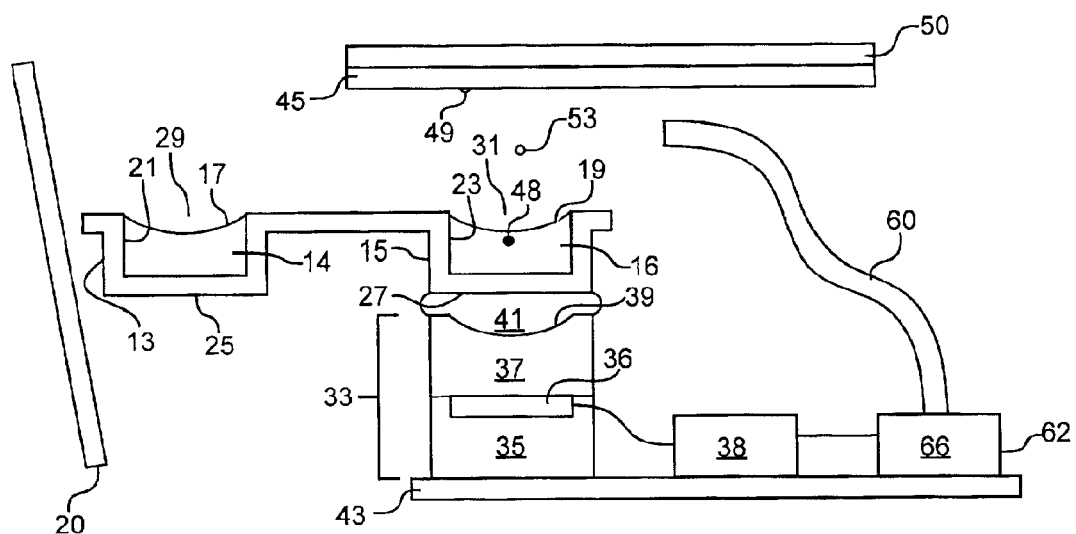
FIG. 2 schematically illustrates in simplified cross-sectional view an embodiment of the inventive device wherein an acoustic ejector is employed as a means for introducing additional fluid into the reservoir from which fluid may dispensed.

FIG. 2 schematically illustrates in simplified cross-sectional view an embodiment of the inventive device wherein an acoustic ejector is employed as a means for introducing additional fluid into the reservoir from which fluid may be dispensed. The device 11 is similar to that illustrated in FIG. 1 in that a first reservoir, indicated at 13, is provided containing a first fluid. In addition, the device 11 also includes an acoustic ejector 33 comprised of an acoustic generator 35 for generating acoustic radiation and a focusing means 37 for focusing the acoustic radiation at a focal point within the fluid from which a droplet is to be ejected, near the fluid surface. Furthermore, a combination unit 38 is provided that both serves as a controller and a component of an analyzer, and the ejector is acoustically coupled to reservoir 13 through indirect contact via acoustic coupling medium 41. However, the device 11 depicted in FIG. 2 includes an additional acoustic ejector 71, similar in construction to the acoustic ejector 33, for ejecting fluid from reservoir 13. The additional acoustic ejector 71 serves as an introducing means 60 that allows fluid to be ejected from an additional reservoir 62 of additional fluid 66 into reservoir 13.

As depicted in FIG. 2, the additional fluid 66 within reservoir 62 has a fluid surface indicated at 67. The additional acoustic ejector 71, like acoustic ejector 33, is comprised of an acoustic generator 73 for generating acoustic radiation and a focusing means 75 for focusing the acoustic radiation at a focal point 68 within fluid 66 near the fluid surface 67. The acoustic generator contains a transducer 74, e.g., a piezoelectric element, commonly shared by an analyzer. As shown, a combination unit 38 is provided that both serves as a controller and a component of an analyzer. The additional ejector 71 is acoustically coupled to fluid 66 in reservoir 62 to eject droplets therefrom via indirect contact between the additional ejector 71 and the external surface of reservoir 62 through coupling medium 69.

As before, the introducing means 60 may be employed to control the composition and/or volume of reservoir 13, for example, to replenish the composition and/or volume of reservoir 13 due to evaporation. In order to eject droplets of fluid from reservoir 62 to reservoir 13, the acoustic generator 73 is activated to produce acoustic radiation that is directed by the focusing means 75 to a focal point 68 near the fluid surface 67 of the reservoir 62. That is, an ejection acoustic wave having a focal point 68 near the fluid surface 67 is generated in order to eject at least one droplet 70 of the fluid, wherein the optimum intensity and directionality of the ejection acoustic wave is selected to result in the appropriate trajectory to travel from reservoir 62 to reservoir 13. It should be noted that there are a number of ways to ensure that droplets ejected from reservoir 62 travel into the reservoir 13. For example, when the reservoirs are stationary, as depicted in FIG. 2, the desired intensity and directionality of the ejection acoustic wave may be selected to ensure that the droplet ejected travels in a trajectory that has both a vertical and horizontal directional vectors relative to the location of the reservoirs. Alternatively, a droplet may be ejected vertically from reservoir 62 and the reservoirs subsequently moved such that the ejected droplet falls into reservoir 13. This has been described, e.g., in U.S. patent application Publication No. 20020064808 for "Focused Acoustic Energy for Ejection Cells from a Fluid," inventors Mutz and Ellson, assigned to Picoliter, Inc. (Mountain View, Calif.); and U.S. patent application Publication No. 20020064809, for "Focused Acoustic Ejection Cell Sorting System and Method," inventors Mutz, Ellson, and Lee, assigned to Picoliter, Inc. (Mountain View Calif.). It should be apparent, then, that aspects of acoustic technology applicable for acoustic dispensation of fluid from a reservoir may also be employed to introduce additional fluid into the reservoir.

While focused acoustic radiation is typically applied to a fluid to eject droplets in a generally upward direction (e.g., as depicted in FIG. 1E and FIG. 2,), it is possible to use focused radiation to eject droplets in a generally downward direction as well. For example, a fluid may be restrained on a lower surface of a substrate through surface forces. As a result, a free surface may be formed below the fluid. By coupling an acoustic ejector to an opposing upper surface of the substrate and activating the ejector, acoustic radiation may be directed to a focal point near the free fluid surface, thereby ejecting one droplet or more droplets in a generally downward direction from the free fluid surface. Similarly, acoustic ejection may be employed to form horizontally directed droplets as well.

Thus, in addition to the above-described devices, the invention provides a method for acoustically controlling the composition and/or volume of a fluid within a reservoir. The method involves at least two steps, a monitoring step and a potential introducing step. The monitoring step involves monitoring a characteristic of a fluid contained in a reservoir, typically without directly contacting the fluid. The introducing step involves introducing additional fluid into the reservoir according to the results of the monitoring step. The method further involves generating acoustic radiation in order to carry out the monitoring step, the introducing step, or both. When acoustic radiation is generated to carry out the monitoring step, the radiation preferably interacts with the fluid contained in the reservoir and is analyzed thereafter to carry out the introducing step. For example, the generated acoustic radiation may be transmitted through the fluid in the reservoir and analyzed thereafter. In some instances, the acoustic radiation may be reflected by a free fluid surface within the reservoir before analysis. In addition, acoustic radiation generation and analysis may be repeated at predetermined periodic intervals to effect substantially continuous monitoring of the fluid. When acoustic radiation is generated to introduce additional fluid into the reservoir, the generated acoustic radiation may be applied to a source of additional fluid in any manner effective to transport it into the reservoir. This may involve fluid ejection or flow from a reservoir, through a nozzle, or using a nozzleless technique.

Typically, additional fluid is introduced in the reservoir so as to maintain the monitored fluid characteristic within a predetermined range of acceptable values for that fluid characteristic. In some instances, additional fluid having substantially the same composition as that of the fluid already contained in the reservoir is introduced into the reservoir. In other instances, additional fluid having a composition different from that of the fluid contained in the reservoir is introduced into the reservoir. The selection of the particular additional fluid to be introduced into the reservoir is discussed below in greater detail.

The method of acoustical regulation is particularly suited for controlling the composition and/or volume of a reservoir from which fluid is dispensed. In some instances, fluid is dispensed from the reservoir before the composition and/or volume of the reservoir are monitored. In other instances, fluid is dispensed after additional fluid has been introduced into the reservoir. Optionally, fluid is acoustically dispensed from the reservoir. This may be carried out, for example, by employing focused acoustic radiation so as to eject fluid from the reservoir. In addition, the monitoring step is carried out according to the dispensation of fluid from the reservoir. For example, the monitoring step may be carried out at least once per occurrence of fluid dispensation. In some cases, the monitoring step is triggered by fluid dispensation.

As discussed above, one or more reservoirs may be provided. To provide modularity and interchangeability of components, it is preferred that any reservoir provided be removable from the device, though integrated or permanently attached reservoirs may be employed as well. When the invention is practiced using a plurality of reservoirs, the reservoirs are generally arranged in a pattern or an array to provide each reservoir with individual systematic addressability. In addition, while each of the reservoirs may be provided as a discrete or stand-alone item, in circumstances that require a large number of reservoirs, it is preferred that the reservoirs be attached to each other or represent integrated portions of a single reservoir unit. For example, the reservoirs may represent individual wells in a well plate. Many well plates suitable for use with the device are commercially available and may contain, for example, 96, 384, 1536, or 3456 wells per well plate. Manufacturers of suitable well plates for use in the employed device include Corning, Inc. (Corning, N.Y.) and Greiner America, Inc. (Lake Mary, Fla.). However, the availability of such commercially produced well plates does not preclude the manufacture and use of custom-made well plates containing at least about 10,000 wells, or as many as 100,000 to 500,000 wells, or more. To facilitate handling of multiple reservoirs, it is preferred that the reservoirs be substantially acoustically indistinguishable from one another.

Furthermore, the material used in the construction of reservoirs should be compatible with the fluids contained therein. Thus, if it is intended that the reservoirs or wells contain an organic solvent such as acetonitrile, polymers that dissolve or swell in acetonitrile would be unsuitable for use in forming the reservoirs or well plates. Similarly, reservoirs or wells intended to contain DMSO should be compatible with DMSO. For water-based fluids, a number of materials are suitable for the construction of reservoirs and include, but are not limited to, ceramics such as silicon oxide and aluminum oxide, metals such as stainless steel and platinum, and polymers such as polyester and polytetrafluoroethylene. For fluids that are photosensitive, the reservoirs and any associated covers may be constructed from an optically opaque material that has sufficient acoustic transparency to permit substantially unimpaired functioning of the device.

Thus, the invention may involve the use of a reservoir containing one or more fluids of virtually any type and amount desired. The fluid may be aqueous and/or nonaqueous. Examples of fluids include, but are not limited to, aqueous fluids (including water per se and water-solvated ionic and non-ionic solutions), organic solvents, lipidic liquids, suspensions of immiscible fluids, and suspensions or slurries of solids in liquids. In addition, the invention is readily adapted for use with immiscible fluids (see, e.g., U.S. patent application Publication No. 20020037375 to Ellson et al.) as well as for use with high temperature fluids (see, e.g., U.S. Pat. Nos. 5,520,715 and 5,722,479 to Oeftering). The invention is particularly suited for controlling the fluid content in a reservoir containing a multi-constituent fluid in which one constituent may be preferentially removed, leaving an increased concentration or proportion of the remaining constituent, as discussed below.

In addition, to reduce the amount of movement and time needed to align the acoustic generator with each reservoir or reservoir well during operation, it is preferable that the center of each reservoir be located not more than about 1 centimeter, preferably not more than about 1 millimeter, and optimally not more than about 0.5 millimeter, from a neighboring reservoir center. These dimensions tend to limit the size of the reservoirs to a maximum volume. The reservoirs are constructed to contain typically no more than about 1 mL, preferably no more than about 1 $\mu$L, and optimally no more than about 1 nL of fluid. This is particularly useful when the fluid involved contains rare or expensive biomolecules, wherein it may be desirable to transfer fluid volumes of about 1 picoliter (pL) or less, e.g., volumes in the range of about 0.025 pL to about 1 pL.

Generally, a single acoustic generator is employed, though a plurality of acoustic generators may be used as well. All acoustic generators employ a vibrational element or transducer to generate acoustic radiation. Often, a piezoelectric element is employed to convert electrical energy into mechanical energy associated with acoustic radiation. When a single acoustic generator is employed, the positioning means should allow for the acoustic generator to move from one reservoir to another quickly and in a controlled manner, thereby allowing fast and controlled scanning of the composition and/or volume of the reservoirs. In order to ensure optimal performance, it is important to keep in mind that there are two basic kinds of motion: pulse and continuous. Pulse motion involves the discrete steps of moving an acoustic generator into position, keeping it stationary while it emits acoustic energy, and moving the generator to the next position; again, using a high performance positioning means with such a method allows repeatable and controlled acoustic coupling at each reservoir in less than 0.1 second. Typically, the pulse width is very short and may enable over 10 Hz reservoir transitions, and even over 1000 Hz reservoir transitions. A continuous motion design, on the other hand, moves the acoustic generator with respect to the reservoirs continuously. Optionally, the substrate will move continuously with respect to the acoustic generator.

As discussed above, the invention may involve the use of acoustic or nonacoustic techniques to monitor a characteristic of a fluid contained in a reservoir. When an acoustic technique is used, the monitoring means may be provided that includes an acoustic generator and an analyzer for analyzing acoustic radiation generated by the acoustic generator. In some instances, the analyzer is positioned in fixed alignment with respect to the acoustic generator. In other instances, the relative position of the analyzer may be altered with respect to the reservoirs. The design and construction of exemplary acoustic monitoring means are described in detail in U.S. patent application Ser. No. 10/010,972. Nonacoustic monitoring may involve, for example, transmission and/or reflection of electromagnetic radiation, movement of mechanical parts, displacement of fluids, and/or execution of controlled chemical reactions. Other fluid characteristic monitoring methods known in the art may be used as well.

Similarly, acoustic or nonacoustic techniques may be used to introduce fluid into the reservoir(s) or dispense fluid from the reservoir(s). As discussed above, nozzleless acoustic ejection may be used as an introducing means or as a dispensing means for transport fluid droplets. Other fluid transport techniques using devices known in the art may be used as well and include, but are not limited to, inkjet printhead (both thermal and piezoelectric), pipettes, capillaries, syringes, displacement pumps, rotary pumps, peristaltic pumps, vacuum devices, flexible and rigid tubing, tubing, valves, manifolds, pressurized gas canisters, and combinations thereof. In short, the dispensing means and introducing means may employ any fluid-transport technology that is discussed herein or is otherwise known in the art.

Furthermore, it will be appreciated that various components of the device may require individual control or synchronization. For example, the ejector positioning means may be adapted to eject droplets from each reservoir in a predetermined sequence associated with an array to be prepared on a substrate surface. Similarly, the substrate positioning means for positioning the substrate surface with respect to the ejector may be adapted to position the substrate surface to receive droplets in a pattern or array thereon. Either or both positioning means (i.e., the ejector positioning means and the substrate positioning means) may be constructed from, for example, motors, levers, pulleys, gears, a combination thereof, or other electromechanical or mechanical means known to one of ordinary skill in the art. It is preferable to ensure that there is a correspondence between the movement of the substrate, the movement of the ejector, and the activation of the ejector to ensure proper array formation.

The monitoring means may be constructed to perform a number of functions. For example, the monitoring means may be adapted to analyze acoustic radiation to determine the volume of fluid in each reservoir. In addition, or in the alternative, the monitoring means may be adapted to analyze acoustic radiation to determine a property of fluid in each reservoir. Fluid properties that can be determined in this manner include, but are not limited to, viscosity, surface tension, acoustic impedance, acoustic attenuation, speed of sound, solid content, and impurity content. As discussed above, such monitoring means may or may not require the use of an acoustic generator.

As discussed above, there are many instances in which there is a need to control the composition and/or volume of a fluid within a reservoir. For example, when a reservoir contains fluid comprised of a solid constituent dissolved in a liquid solvent, preferential removal of the solvent, e.g., through evaporation, increases the solid constituent concentration. This may in turn increase the viscosity of the fluid contained in the reservoir, and, in some cases, result in precipitation of the solid constituent out of solution. Precipitation of solid particles out of solution may, for example, clog nozzles of inkjet printheads as well as obstruct fluid transfer tubing. In addition, in the case of nozzleless fluid ejection using focused acoustic radiation, evaporation of a solvent from a fluid containing a solid solute has been found to be a major cause of variations in the repeatability and quantity of solid constituent transfer.

Figure 3:
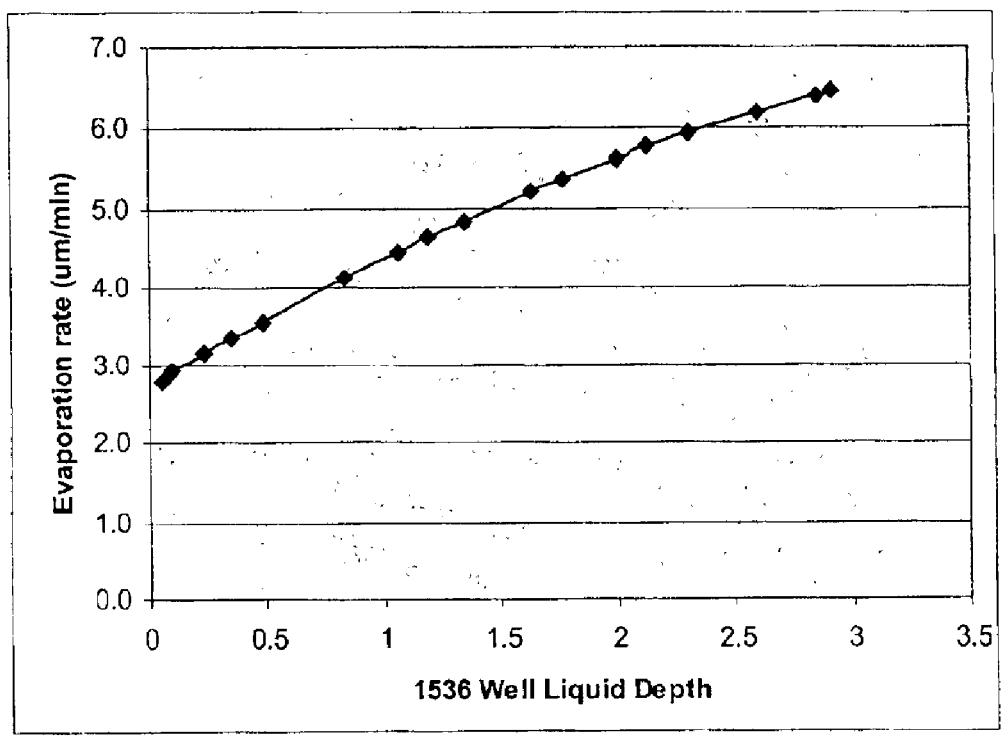
FIG. 3 graphically depicts the measured rate of fluid height change as plotted against the fluid height in a well of a 1536 unit well plate.

When the device depicted in FIG. 1 is employed, there are at least four modes in which fluid content in a reservoir may be changed, and the monitoring means is typically suitable for monitoring for any change in the content of a reservoir as a result of such fluid transfer modes. First, fluid may be introduced into the reservoir through the introducing means. Second, fluid may be removed from the reservoir through ejection using focused acoustic radiation. Third, fluid may leave the reservoir through evaporation. An example of acoustically monitoring the evaporation of a single constituent fluid, i.e., water, from a single well in a 1536 unit well plate is shown in FIG. 3. FIG. 3 graphically depicts the measured rate of fluid height change as plotted against the fluid height in a well of a 1536 unit well plate. The height of the fluid in the well was measured through acoustic microscopy. A fourth possibility is that the fluid within the reservoir may absorb atmospheric gases such as moisture vapor. This is typically the case when the fluid in the reservoir contains a hydrophilic constituent, e.g., DMSO. In such a case, additional DMSO may be introduced into the reservoir to ensure that absorbed water does not exceed a certain concentration.

With multiple-constituent fluids, the proportions of the constituents may vary according to the fluid transfer mode. In the case of a fluid that contains a solvent and a solute, if the initial concentration of the solution in the reservoir is known, then the mass of the solute may be determined by converting the acoustically measured fluid volume in the reservoir. Evaporation of the solvent does not change the mass of the solute, and the effect of evaporation on the volume of fluid in the reservoir can be tracked acoustically. The loss of solute via droplet ejection may be calculated from the volume of the drop ejected and the concentration of the solution at the time of ejection. Thus, for example, additional solvent may be introduced into the reservoir to maintain the concentration of solute in the reservoir to compensate for solvent evaporation. In addition, it follows that a dilute solution of the solute may be introduced into the reservoir to ensure that the volume of fluid in the reservoir and the concentration of the solute in the fluid are maintained at a constant level. Similarly, absorption of a solute-free fluid, e.g., atmospheric water vapor, does not change the mass of solute, and the effect of absorption on the volume of fluid in the reservoir can be tracked acoustically. The loss of solute via droplet ejection may be calculated from the volume of the drop ejected and the concentration of the solution at the time of ejection. Thus, for example, additional fluid containing a high concentration of solute may be introduced into the reservoir to maintain the concentration of solute in the reservoir to compensate for solvent evaporation.

Thus, if a reservoir contains a very dilute solution comprising water and an oligonucleotide, then as the water evaporates, the concentration of the oligonucleotide rises until the solubility limit is reached. In order to form reproducible features of oligonucleotide on a substrate, it is often preferable to create spots of the same size and identical concentrations to get the same signal intensity in the spots. Thus, the invention provides a method for maintaining drop volume consistency and signal intensity within the formed spot. This may involve, for example, ejecting droplets of substantially identical volume and/or composition at designated sites on a substrate surface.

A more complex case occurs when two miscible solvents with different vapor pressures are present in the reservoir, since the evaporation rates for the two constituents will differ. This difference in evaporation rate leads to the more rapid depletion of one solvent relative to the other, and hence, would require some independent control over the volumes of each solvent introduced into the reservoir to replenish that lost through evaporation. The measured acoustic properties of the desired proportions of the solvents in the binary mixture could also be used to audit and control the reservoir mixture. Fluid content assessment could, in some instances, be taken upon the initial filling of the well. It should be noted that these mass balance considerations may be described using known equations.

Similarly, the invention may be employed to control the composition and/or volume of immiscible fluids within a reservoir. The use of focused acoustic radiation in conjunction with immiscible fluids in a reservoir has been described in U.S. patent application Publication No. 20020037375 to Ellson et al. and in U.S. patent application Ser. No. 10/112, 693 entitled "Use of Immiscible Fluids in Droplet Ejection through Application of Focused Acoustic Energy," filed Mar. 28, 2002, inventors Ellson, Mutz and Foote. As described in these applications, one immiscible fluid may be used to suppress evaporation of another fluid. In addition, such fluids may form an upper and a lower layer in a reservoir The invention may involve the individual monitoring and/or control over each of the immiscible fluids.

For example, when the immiscible fluids form an upper and a lower layer, the upper layer may serve to encapsulate droplets ejected from the lower layer. However, as droplets of the fluid from the lower layer are ejected through the upper layer, fluid depletion of the upper layer may be occur. In turn, the thickness of the encapsulating layer may decrease. Thus, invention may be employed to maintain the upper layer of fluid within a range of appropriate thicknesses by monitoring for upper layer fluid depletion and introducing an additional fluid to compensate for such fluid depletion.

Alternatively, the ratio of the thickness of the upper fluid layer to the lower fluid layers may increase as fluid from the lower layer is preferentially ejected from a reservoir. When the reservoir exhibits a tapered profile, the thickness of the upper layer may increase as fluid is ejected from the lower layer. That is, this may occur when the overall fluid level drops at a rate such that the cross-sectional area of the reservoir at the fluid surface decreases to an extent that cannot be compensated by the rate of fluid removal from the upper layer. In such a case, additional fluid may be introduced into the lower layer or removed from the upper layer.

As discussed above, the invention may be used to in conjunction with fluids that are inhomogeneous and/or contain multiple phases of materials as well as with fluids that are homogeneous. However, it should be noted that some homogeneous fluids may become destabilized and become inhomogeneous under certain circumstances and vice versa. For example, focused radiation may cause local perturbations in a reservoir of fluid, which, in turn, result in the formation of a separate phase in the fluid. This may involve, for example, the nucleation and growth of a bubble out of a fluid from solute gas. Similarly, application of focused radiation may serve to homogenize an otherwise inhomogeneous fluid. Thus, in another aspect, the invention may be used in conjunction with the application of focused radiation to homogenize or dehomogenize a fluid in a reservoir.

It is to be understood that, while the invention has been described in conjunction with the preferred specific embodiments thereof, the foregoing description is intended to illustrate and not limit the scope of the invention. Other aspects, advantages, and modifications will be apparent to those skilled in the art to which the invention pertains.

All patents, patent applications, journal articles, and other references cited herein are incorporated by reference in their entireties.

We claim:

1. A device for controlling the composition and/or volume of a fluid within a reservoir, comprising:
   an acoustic generator for generating acoustic radiation;
   a reservoir containing a fluid comprised of a plurality of constituents, wherein the fluid may deviate from a desired concentration of a selected constituent;
   an acoustic coupling medium coupled to the acoustic generator;
   a means for monitoring at least one characteristic of a fluid contained in the reservoir, wherein the monitoring means does not directly contact the fluid contained in the reservoir;
   a source of the selected constituent; and
   a means for introducing the selected constituent from the source into the reservoir taking into account the at least one characteristic monitored by the monitoring means so as to establish, maintain, or restore the fluid in the reservoir at the desired concentration of the selected constituent,
   wherein the acoustic generator is associated with the monitoring means, the introducing means, or both.

2. The device of claim 1, wherein the reservoir contains no more than about 1 mL of fluid.

3. The device of claim 2, wherein the reservoir contains no more than about 1 µL of fluid.

4. The device of claim 3, wherein the reservoir contains no more than about 1 nL of fluid.

5. The device of claim 1, wherein the acoustic generator is associated with the monitoring means and the monitoring means further comprises an analyzer for analyzing acoustic radiation generated by the acoustic generator.

6. The device of claim 5, wherein the analyzer is positioned to receive acoustic radiation generated by the acoustic generator and transmitted through the fluid contained in the reservoir.

7. The device of claim 6, wherein the analyzer is positioned to receive acoustic radiation reflected by the free surface of the fluid contained in the reservoir.

8. The device of claim 7, wherein the analyzer comprises a component common to the acoustic generator.

9. The device of claim 8, wherein the component common to the analyzer and the acoustic generator is a piezoelectric element.

10. The device of claim 1, wherein the at least one fluid characteristic monitored by the monitoring means includes volume.

11. The device of claim 1, wherein the at least one fluid characteristic monitored by the monitoring means includes viscosity.

12. The device of claim 1, wherein the at least one fluid characteristic monitored by the monitoring means includes surface tension.

13. The device of claim 1, wherein the at least one fluid characteristic monitored by the monitoring means includes acoustic impedance.

14. The device of claim 1, wherein the at least one fluid characteristic monitored by the monitoring means includes acoustic attenuation.

15. The device of claim 1, wherein the at least one fluid characteristic monitored by the monitoring means includes solid content.

16. The device of claim 1, wherein the at least one fluid characteristic monitored by the monitoring means includes impurity content.

17. The device of claim 1, wherein the monitoring means is adapted to monitor the fluid characteristic at predetermined intervals.

18. The device of claim 17, wherein the predetermined intervals are periodic.

19. The device of claim 1, wherein the acoustic generator is associated with the introducing means.

20. The device of claim 1, further comprising a means for dispensing fluid from the reservoir.

21. The device of claim 20, wherein the acoustic generator is associated with the dispensing means and the monitoring means.

22. The device of claim 21, wherein the dispensing means further comprises an acoustic ejector.

23. The device of claim 22, wherein the acoustic ejector further comprises a means for focusing acoustic radiation generated by the acoustic generator.

24. The device of claim 1, comprised of a single acoustic generator.

25. The device of claim 1, wherein the at least one fluid characteristic monitored by the monitoring means includes constituent content.

26. A method for controlling the composition and/or volume of a fluid within a reservoir, comprising the steps of:
  (a) monitoring a characteristic of a fluid contained in a reservoir without directly contacting the fluid, wherein the fluid is comprised of a plurality of constituents and the fluid may deviate from a desired concentration of a selected constituent; and
  (b) introducing the selected constituent from a source of the selected constituent into the reservoir taking into account the fluid characteristic monitored in step (a) to establish, maintain, or restore the fluid in the reservoir at the desired concentration of the selected constituent,
  wherein step (a), step (b), or both are carried out by generating acoustic radiation and transmitting the acoustic radiation through an acoustic coupling medium into the reservoir for step (a) and into the source for step (b).

27. The method of claim 26, wherein step (a) comprises:
  (a') generating acoustic radiation such that the radiation interacts with the fluid contained in the reservoir; and
  (a") analyzing the acoustic radiation after interaction with the fluid to assess the fluid characteristic for use in step (b).

28. The method of claim 27, wherein the radiation interacts by transmission through the fluid.

29. The method of claim 28, the transmitted radiation is analyzed after the acoustic radiation is reflected by the free fluid surface within the reservoir.

30. The method of claim 27, wherein steps (a') and (a") are repeated.

31. The method of claim 30, wherein steps (a') and (a") are repeated at predetermined intervals.

32. The method of claim 31, wherein the intervals are periodic.

33. The method of claim 26, wherein step (b) comprises applying acoustic radiation to the source of the selected constituent in a manner effective to transport the selected constituent into the reservoir.

34. The method of claim 26, further comprising step (c) dispensing fluid from the reservoir.

35. The method of claim 34, wherein step (c) is carried out before step (a).

36. The method of claim 34, wherein step (c) is carried out after step (b).

37. The method of claim 34, wherein step (c) comprises acoustically dispensing fluid from the reservoir.

38. The method of claim 37, wherein step (c) comprises acoustically ejecting fluid from the reservoir.

39. The method of claim 38, wherein step (c) comprises employing focused acoustic radiation so as to eject fluid from the reservoir.

40. The method of claim 39, wherein step (c) is repeated.

41. The method of claim 40, wherein fluid is ejected in the form of droplets.

42. The method of claim 41, wherein the droplets are of substantially identical volume.

43. The method of either claim 41 or claim 42, wherein the droplets are of substantially identical composition.

44. The method of claim 41, wherein the droplets are deposited on a substrate surface.

45. The method of claim 44, wherein the droplets deposited on the substrate surface form an array.

46. The method of claim 40, wherein step (a) is carried out at least once per occurrence of step (c).

47. The method of claim 46, wherein step (a) is triggered by the occurrence of step (c).

48. The method of claim 26, wherein step (b) is carried out so as to maintain the monitored fluid characteristic within a predetermined range of acceptable values for the fluid characteristic.

49. A device for dispensing fluid from a reservoir, comprising:
  an acoustic generator for generating acoustic radiation;
  a reservoir containing a fluid comprised of a plurality of constituents, wherein the fluid may deviate from a desired concentration of a selected constituent;
  an acoustic coupling medium coupled to the acoustic generator;
  a means for controllably dispensing fluid from the reservoir;
  a means for monitoring a characteristic of the fluid contained in the reservoir, wherein the monitoring means is external to the reservoir and does not directly contact any fluid contained in the reservoir;
  a source of the selected constituent; and
  a means for introducing the selected constituent from the source into the reservoir based at least in part on the characteristic monitored by the monitoring means so as to establish, maintain, or restore the fluid in the reservoir at the desired concentration of the selected constituent,
  wherein the acoustic generator is associated with at least one the dispensing means, the monitoring means, and the introducing means.

50. The device of claim 49, wherein the acoustic generator is associated with the dispensing means.

51. The device of claim 49, wherein the acoustic generator is associated with the monitoring means.

52. The device of claim 49, wherein the acoustic generator is associated with the introducing means.

53. The device of claim 49, wherein the acoustic generator is associated with at least two of the dispensing means, the monitoring means, and the introducing means.

54. The device of claim 53, the acoustic generator is associated with the dispensing means and the monitoring means.

55. The device of claim 54, comprised of a single acoustic generator.

56. A device for controlling the composition and/or volume of a plurality of fluid reservoirs, comprising:
  an acoustic generator for generating acoustic radiation;
  a plurality of reservoirs each containing a fluid, wherein the fluid contained in at least one reservoir is comprised of a plurality of constituents and may deviate from a desired concentration of a selected constituent;
  an acoustic coupling medium coupled to the acoustic generator;
  a means for monitoring a characteristic of the fluid contained in each reservoir, wherein the monitoring means is external to the reservoirs and does not directly contact the fluid within the reservoirs;
  a source of the selected constituent; and
  a means for introducing the selected constituent from the source into the at least one reservoir based at least in part on the characteristic monitored by the monitoring means so as to establish, maintain, or restore the fluid in the at least one reservoir at the desired concentration of the selected constituent, wherein acoustic generator is associated with the monitoring means, the introducing means, or both.

57. The device of claim 56, wherein the monitoring means is adapted to monitor the characteristic of fluid contained in a single reservoir at a time.

58. A method for controlling the composition and/or volume of a plurality of fluid reservoirs, comprising the steps of:

(a) monitoring a characteristic of a fluid contained in a reservoir without directly contacting the fluid within the reservoir, wherein the fluid is comprised of a plurality of constituents and the fluid may deviate from a desired concentration of a selected constituent;

(b) introducing additional fluid from a source into the reservoir taking into account the fluid characteristic monitored in step (a) so as to establish, maintain, or restore the fluid in the reservoir at the desired concentration of the selected constituent; and (c) repeating steps (a) and (b) for a different reservoir selected from the plurality of reservoirs, thereby controlling the composition and/or fluids in the reservoirs, wherein step (a), step (b), or both are carried out by generating acoustic radiation and transmitting the acoustic radiation through an acoustic coupling medium into the reservoir for step (a) and the source for step (b).

59. A device for dispensing fluid from a plurality of reservoirs, comprising:

an acoustic generator for generating acoustic radiation;

a plurality of reservoirs each containing a fluid, wherein the fluid in at least one reservoir is comprised of a plurality of constituents and may deviate from a desired concentration of a selected constituent;

an acoustic coupling medium coupled to the acoustic generator;

a means for controllably dispensing a fluid from the reservoir;

a means for monitoring a characteristic of the fluid contained in each reservoir;

a source of the selected constituent; and a means for introducing the selected constituent from the source into the at least one reservoir based at least in part on the characteristic monitored by the monitoring means so as to establish, maintain, or restore the fluid in the at least one reservoir at the desired concentration of the selected constituent, wherein the acoustic generator is associated via the acoustic coupling medium with at least one of the dispensing means, the monitoring means, and the introducing means.

60. A device for controlling the composition and/or volume of a fluid within a reservoir, comprising:

an acoustic generator for generating acoustic radiation;

a reservoir containing a fluid comprised of a plurality of constituents;

an acoustic coupling medium coupled to the acoustic generator;

a means for monitoring preferential removal of at least one preferentially removable constituent from the reservoir;

a source of additional fluid comprised of the at least one preferentially removable constituent; and a means for introducing additional fluid from the additional fluid source into the reservoir in response to any preferential removal of the at least one constituent as monitored by the monitoring means so as to establish, maintain, or restore the fluid in the reservoir at a desired concentration of the selected constituent, wherein the acoustic generator is associated with the monitoring means, the introducing means, or both.

61. A method for controlling the composition and/or volume of a fluid within a reservoir, comprising the steps of:

(a) monitoring for preferential removal of at least one preferentially removable constituent from a reservoir containing a fluid comprised of a plurality of constituents; and (b) introducing additional fluid comprised of the at least one preferentially removable constituent from a source into the reservoir in response to any preferential removal of the at least one constituent as monitored in step (a) to control the composition and/or volume of the fluid reservoir so as to establish, maintain, or restore the fluid in the reservoir at a desired concentration of the selected constituent, wherein step (a), step (b), or both are carried out by generating acoustic radiation and transmitting the acoustic radiation through an acoustic coupling medium into the reservoir for step (a) and the source for step (b).

* * * * *